US006800062B2

United States Patent
Epley (10) Patent No.: US 6,800,062 B2
(45) Date of Patent: Oct. 5, 2004

(54) COMPREHENSIVE VERTIGO MANAGEMENT

(75) Inventor: John M. Epley, Portland, OR (US)

(73) Assignee: Epley Research, L.L.C., Portland, OR (US)

( * ) Notice: Subject to any disclaimer, the term of this patent is extended or adjusted under 35 U.S.C. 154(b) by 96 days.

(21) Appl. No.: 10/188,564

(22) Filed: Jul. 3, 2002

(65) Prior Publication Data

US 2004/0006287 A1 Jan. 8, 2004

(51) Int. Cl.$^7$ .............................................. A61B 13/00
(52) U.S. Cl. ...................................................... 600/558
(58) Field of Search ................................ 600/595, 552, 600/546; 359/480, 831; 340/407.1; 73/432.1, 865.6; 2/428; 434/46, 30, 55, 59

(56) References Cited

U.S. PATENT DOCUMENTS

| | | |
|---|---|---|
| 3,258,008 A | 6/1966 | Vulliet-Durand |
| 3,583,794 A | 6/1971 | Newman |
| 3,716,046 A | 2/1973 | Janeke |
| 4,102,564 A | 7/1978 | Michael |
| 4,320,768 A | 3/1982 | Ledley et al. |
| 4,474,186 A | 10/1984 | Ledley et al. |
| 4,698,564 A | 10/1987 | Slavin |
| 4,710,128 A * | 12/1987 | Wachsmuth et al. .......... 434/46 |
| 4,738,269 A | 4/1988 | Nashner |
| 4,818,097 A | 4/1989 | Linde |
| 4,830,024 A | 5/1989 | Nashner et al. |
| 4,988,183 A | 1/1991 | Kasahara et al. |
| 5,042,910 A * | 8/1991 | Dolezal ....................... 359/480 |
| 5,285,685 A * | 2/1994 | Chelette ..................... 73/432.1 |
| 5,303,715 A | 4/1994 | Nashner et al. |
| 5,517,021 A | 5/1996 | Kaufman et al. |
| 5,942,954 A | 8/1999 | Galiana et al. |
| 2002/0151818 A1 * | 10/2002 | Watt et al. ................... 600/552 |

* cited by examiner

Primary Examiner—Eric F. Winakur
Assistant Examiner—Brian Szmal
(74) Attorney, Agent, or Firm—Jon M. Dickinson, P.C.; Robert D. Varitz, P.C.

(57) ABSTRACT

A comprehensive vertigo management system and methodology is provided which employs a spatial maneuvering device, preferably under computer control, to orient a subject selectively differently in space, thus to create vestibular activity which is directly related to spatial motion (including acceleration) and/or orientation. Data is collected relating to such orientation and activity, along with certain subject-introduced reaction data in certain instances and video-camera data, and fed to a computer which cooperates in presenting an intuitive visual and pictorial correlation that enables physician diagnosis, treatment and rehabilitation regarding elements of dysfunction of the subject's vestibular system.

18 Claims, 3 Drawing Sheets

COMPREHENSIVE VERTIGO MANAGEMENT

BACKGROUND AND SUMMARY OF THE INVENTION

1. Introductory Information

This invention relates to a comprehensive, computer-based, medical method and apparatus for diagnosing and treating human disorders involving symptoms of dizziness, vertigo and imbalance. In particular, it relates to a unique and remarkably versatile system and methodology for examining, and where appropriate treating, and rehabilitating (reconditioning), the usual complex vestibular-system source of such symptoms.

As will be more fully elaborated below, vertigo, imbalance and related symptoms are often caused by, or related to, dysfunction in the central nervous system with regard to processing of visual, vestibular and somatosensory inputs. Thus, in some cases, and in relation to the utility of the present invention for rehabilitation, vestibular therapy, as performed by the invention, is directed toward retraining, reconditioning and habituating central nervous system processing in this regard. The methods of accomplishing this are many, but, as will be seen, may involve exercises that include isolating or denormalizing certain ones of the visual, vestibular and somatosensory inputs while exercising others. The present invention can readily carry out many of these exercises or tasks, under control of a computer, an operator, or the subject, or combinations thereof, via the control and processing structures and modalities offered and enabled by the invention. It can carry out exercises that consist of isolating or denormalizing certain of the visual, vestibular and somatosensory inputs, or others that encourage the coordination of these inputs. The system and methodology of the invention can prescribe the tasks, customize the character and complexity of the exercises to the subject, carry them out and document progress.

All of such examining, treating and/or rehabilitating activities are referred to herein as vertigo management. The system and method of the invention offer an opportunity to perform, in a unified setting, a very wide range of tasks relating to vestibular-system issues, including several novel tasks, such as real-time event-following correlation, not heretofore available.

2. Background Information

As was mentioned briefly above, the vestibular-system medical issues to which the present invention addresses its focus are complex. The background information which now follows generally outlines these issues, and sets the stage for a clear understanding about how the present invention deals elegantly with this complexity in a clearly intuitive versatile, flexible and straight-forward manner.

Dizziness, including vertigo and imbalance, is one of the most common complaints presented to the physician. Although these symptoms may be caused by a variety of abnormal conditions affecting either the peripheral or central nervous systems, the cause can most commonly be traced to abnormalities involving the vestibular endorgans in the inner ear or, less frequently, to their associated neural pathways in the brainstem or cerebellum. The vestibular endorgans are mechano-transducers that normally sense either angular or linear acceleration of the head. Thus, progress in diagnosing and treating the above disorders has been very dependent upon the ability to observe and quantify the reflex output of these vestibular sensors, and/or the subjective responses thereto.

The sensors of angular acceleration, which provide the percept of rotation in space in any plane, are the semicircular canals (also referred to as SC and SCC), which are located with three on each side within the inner ear, and oriented orthogonally to each other. Each semicircular canal acts as a transducer of rotation in the plane of its orientation. It contains fluid that, due to inertia, lags angular accelerations or decelerations of the head in the plane of the canal, and thereby actuates a sensor of fluid displacement, the cupula. This provides information via neural pathways to the brain stem that is carried via a reflex arc to the eye muscles, called the vestibulo-ocular reflex (VOR). During rotations of the head, this reflex keeps the eyes oriented in space via a counter-rotation until the eyeball reaches a certain point, whereupon there is a quick correction in the opposite direction called a saccade. When repetitive, this results in an involuntary jerking motion of the eyes called nystagmus that occurs in the plane of the semicircular canals that generate it. By observing this nystagmus under various conditions one can determine whether the semicircular canals are functioning normally and, if not, which canal is dysfunctional and the nature of the dysfunction. Also, the nystagmus can be followed in the course of treatment to monitor effectiveness. Dysfunction of the semicircular canals results mainly in symptoms of vertigo.

Quantitative assessment of the VOR under various conditions is carried out as a standard battery of tests known as nystagmography. When eye electrodes are used to detect eye movement, it is called electronystagmography (ENG). When video technology is used to detect eye movement, it is called videonystagmography (VNG). Testing is usually carried out in a light-obscuring environment in order to minimize the effects of optic fixation on the suppression of nystagmus. To varying degrees, nystagmus can also be suppressed by lack of alertness, certain drugs and habituation.

The standard ENG/VNG test battery includes a few standard head positions that are intended to provide an analysis of positional vertigo. Unfortunately, these test positions were standardized prior to the development of new knowledge regarding the causes of positional vertigo, such that they are not the ideal anatomical positions for obtaining useful information. For instance, certain key positions have been found where certain types of positional vertigo are aggravated and where the associated nystagmus is most easily detected, yet none of these is included in the standard test battery. Thus, new methods of investigating the causes of positional nystagmus and vertigo call for new standard positions for screening purposes, plus the triggering of more definitive tests when indicated, some of which require that the patient be maneuvered in ways that are most effectively practiced with a multi-axial positioning apparatus. In addition, nystagmus data is typically acquired and analyzed in small segments, completely ignoring the nystagmus occurring during intervening periods and transition moves. Inasmuch as the nystagmus occurring in a particular test position will be dependent upon numerous factors, such as the rapidity and method of the just-preceding transition maneuver, the time lapse after the test position is reached until the data-acquisition run is commenced, the exact angles of the test positions, etc., the usual ENG/VNG test battery as now generally carried out is not, in reality, standardized. Nor does it make optimum use of the data available.

The presence of many factors, some of which may be quite subtle, and of various time-changing and simultaneously interacting conditions, such as subject motions to, from and beyond various relevant spatial orientations, casts, the practice of vestibular-system investigation, treatment and rehabilitation with a need and desire for sophisticated real-time correlation, and succinct and cogent presentation of relevant unfolding facts and vestibular-system behaviors. In particular, it dictates for the need for thoughtful computer processing, and intuitive and quickly graspable situation presentation, preferably in clear visual (and especially pictorial) form, to aid the investigating/treating/ rehabilitating physician, or other attending party. Subtle, nuanced responses to test, treatment and rehabilitation protocols, often interactively related to other simultaneous such responses, challenge accurate observability, and can easily escape significant notice, even to skilled observers whose attentions may be widely divided because of the attendant complexities of changing test parameters and subject responses. Such subtleties, however, will not escape the grasp of an appropriately employed computer—a grasp which can, and as will be explained below in accordance with the present invention, quickly and unfailingly furnish comprehensive presentations and analysis of interactive, correlative vestibular data.

What is needed, accordingly, is a method of carrying out the indicated screening and definitive tests, that can be automated and programmed to carry out and report intuitively on all tests and positionings in exactly the same manner and with the same timing each time employed.

Incidentally, where references are made herein to positions, positionings, orientations, and spatial orientations, those references are intended to involve either a subject's static disposition in three-dimensional space, and/or a subject's dynamic movement, in any direction or plane of motion, toward, through, and/or beyond one, or several, of such dispositions Continuing with a general mention regarding where improvements and advances are welcome, it is also very desireable to implement tests and positionings, such as those outlined above, in a setting which is capable of interjecting certain more definitive tests when so indicated by the screening tests, that can perform examining approaches (tests) that are physiologically more meaningful and useful in diagnosing, treating and rehabilitating a subject, that can acquire data in a continuum throughout a procedure session, and that can, through careful programming, accomplish these tasks in as short a time as possible. Inasmuch as this can create a much larger volume of data than prior methods, structure and methodology must also be available that selects, analyzes and displays the data in a brief and understandable summary.

In the human vestibular system, the sensors of linear acceleration, the otolithic organs, called the utricle and saccule, are located on each side in the inner ear. Each is made up of a layer of heavy particles that is attached to hair cells that can, when stimulated, initiate a neural discharge. When the head is placed in various positions relative to gravity, or moves linearly in various directions, the resulting change in the inertio-gravitational vector acting upon the particles presents changing forces of strain that modulate the neural discharge of the attached hair cells. The resulting neural input leads to the brain stem, thence to the spinal nerves, and finally to the muscles of postural control in what is called the "vestibulo-spinal reflex" (VSR). Simultaneously, at a higher level, there is a subjective sense of the inertio-gravitational vector, called graviception, that in a normal subject is accurate to within a few degrees.

Abnormal conditions adversely affecting the otolithic organs cause mainly symptoms and signs of imbalance. This imbalance of otolithic origin results from either unstable neural input from an otolithic organ, or organs, or a bilateral deficit. Unstable neural input results from otolithic function that is either recently reduced from the normal, or is distorted from the normal input. This distorted neural input usually results from aberrant receptivity of the otolithic organ to non-gravitational forces such as sound and changing intralabyrinthine pressure. Central compensation generally takes place adequately over time for the reduced form if it is unilateral and becomes stable, but compensation is delayed or not forthcoming in response to the distorted form because of its persistent instability. Thus, the distorted form is by far the more common cause of chronic vertigo. It is seen frequently as the mechanism of post-traumatic vertigo.

My research has indicated that a quantifiable assessment of the distorted neural input arising as a consequence of aberrant receptivity of an otolithic organ can be accomplished in two ways: (1) by determining the adverse postural effects of either sound or changing intralabyrinthine pressure, as can be ascertained in the standing subject by observing, directly or by posturography, an increase in sway or a tendency to fall; and (2) by determining the adverse subjective effects of either sound or changing intralabyrinthine pressure on the directional perception of the inertio-gravitational vector. Such introduced sound and pressure stimuli perform what is referred to herein as denormalization of one or more of a subject's perception capabilities. The problem with relying on adverse postural effects for this purpose, as by posturography, is that test subjects are usually acutely aware of their recent postural misperceptions that have resulted in abnormal sway or fall in a particular direction, and can quickly compensate for these misperceptions to some degree. Thus, if air pressure, or sound, that is presented to an ear canal of a standing subject with eyes closed were to cause a sway or fall in a particular direction, the next time the same stimulus is presented the subject will habitually tend to compensate by counteracting the sway or fall. This is because, on the first trial, the subject received somatosensory feedback from the feet and postural muscles indicating that involuntary sway or a fall, in a particular direction, took place. This tendency to compensate results in limited repeatability, and thus questionable reliability, of such a test using postural control as a measure. If, instead, both before (control) and during presentation of air pressure, or sound, to an ear canal, a test subject indicates his or her subjective perception of the gravity vector (graviception) by reorienting a visual object, and the subject cannot see the surround to obtain visual cues of the true gravitational vector, then the subject will not know if, or by how much, he or she deviated from the control in the subject-given indication of the gravity vector, and so cannot compensate for the deviation on the next trial. This novel graviception method results in greater repeatability and reliability, and its application in the present invention is discussed below.

In the practice of the present invention, the above mentioned "visual object" may be any image or physical object that provides a reference to gravity that can be presented to the subject combined with an input device—button, lever, joystick, computer mouse, trackball, etc.—by way of which the subject responds to that image or object and thus introduces a subjective-response (voluntary) data-stream into a computer.

Many subjects with vertigo symptoms complain of aggravation of their symptoms by loud sound, or by conditions that are known to impart pressure change to the intralabyrinthine fluids. Aberrant receptivity of the labyrinth to sound or intralabyrinthine pressure change can occur in either the semicircular canals, thereby adversely impacting the VOR system and producing nystagmus, or the otolithic organs, thereby adversely impacting the VSR system and producing abnormal postural effects and altered gravitational perception. The latter condition, involving the VSR system, occurs far more frequently, yet standard testing of the effect of sound or intralabyrinthine pressure change involves only observation of the eyes. Thus, in the standard Hennebert (pressure) test and Tullio (sound) tests, the subject is seated, and the clinician only observes the eyes, either directly or with the assistance of magnification or electronic means, for abnormal nystagmus. Therefore, a method is needed for quantifying and localizing the effects of sound and intralabyrinthine pressure change on the VSR arc by monitoring their effects on postural control, or better yet, on gravitational perception.

The usual method (Halmagyi) of assessing a subject's gravitational perception involves a seated subject in a light-proof enclosure who is given the task of repositioning a light-bar to the perceived visual vertical in the roll plane when the chair in which the subject is seated is tilted in the roll plane. This method has the disadvantage that no measurement is carried out in the pitch plane, although research indicates that distorted gravitational perception involves the pitch plane at least as much, and as often, as the roll plane.

In the present state-of-the-art, quantitative information on the status of both the VOR and the VSR requires two separate devices, taking up more space in the vestibular laboratory and adding to expense. In addition, several valuable existing tests that have not been utilized significantly outside of research laboratories because of the expense involved in the equipment to perform each test separately would ideally be integrated into one comprehensive system, and this consideration is very effectively addressed by the present invention.

Furthermore, state-of-the-art testing for position-evoked nystagmus is carried out largely in a few static positions, with conditions and convenience not allowing a more dynamic set of test maneuvers. In fact, the nystagmus patterns that subjects display in relation to introduced maneuvers are sometimes so complex that interpretation in real time is very difficult using present methods. Significant difficulty here arises, among other reasons, from the likelihood that the observing party's attention is divided and scattered, rather than being condensed to enable clearer interpretation focus.

One example of this is seen with vestibular lithiasis, or benign paroxysmal positional vertigo and different variants, whereby abnormal particles in the semicircular canals render the canals sensitive to linear acceleration, including gravitation, creating symptoms of vertigo in response to a position change of the head relative to gravity. These conditions are very common, and can often be improved or corrected by repositioning maneuvers whereby the particles are moved, via sequential positioning of the subject's head, and optional induced head oscillation, to an area of the labyrinth where they no longer produce abnormal responses. Most subjects with these conditions can be treated successfully by canalith repositioning maneuvers, including variations thereof collectively known as particle repositioning maneuvers. Such maneuvers are designed to cause migration of aberrant particles to an area of the labyrinth where they no longer affect the dynamics of the semicircular canals.

These maneuvers are typically carried out manually on a table with a high success rate in the less complicated cases. However, for the more complicated cases, optimal performance of these maneuvers requires ongoing and more challenging, real time observation and analysis of nystagmus. The nystagmus pattern may rapidly change during the performance of maneuvers, sometimes indicating the need for a critical change in strategy in the middle of the maneuver sequence. Present methods, whereby the subject is manually positioned on a table, have difficulty in accomplishing this. Further, the manual maneuvers for testing and treatment may introduce risk because of the abnormal bending and stretching of the neck and back that is required for their accomplishment. Such abnormal bending and stretching of the neck and back has been known to produce thrombosis of the neck vessels and strokes.

In addition, and as was mentioned above, nystagmus patterns that subjects may display in response to various maneuvers may be complex, and rapidly changing, and this may occur in situations where immediate interpretation is often required. Such a requirement usually becomes more acute when the need for a change in strategy is indicated (e.g. a conversion of the causative particles from the posterior to the horizontal canal, or the development of a jamming of the particles). In this kind of setting, there is a clear need for the operator, during the entire sequence of maneuvers, to envision the 3-D orientation with respect to space and gravity of the semicircular canals inside the head, and the apparent position of the particles within those canals. This is difficult, inter alia, because of the constant changing orientation in space of the subject during maneuvers, whether manual or automated. The operator task is even more deeply challenging in this regard where, in addition to the need for clear visualization of the real three-dimensional situation at hand, the operator needs to relate this situation quickly and effectively to the presentation of subject vestibular behavior, so as to advance an investigation, and/or to implement an appropriate treatment or rehabilitation maneuver.

Carrying out manual repositioning maneuvers on a table has many other limitations, such as difficulty moving heavy subjects, or those with back and neck problems. Also, it is often difficult to observe the nystagmus while physically maneuvering the subject. It is difficult to replicate exactly or to standardize manual maneuvers. Another limitation of a table for particle repositioning is that there is occasional need for a 360-degree maneuver, in either the yaw or the pitch plane of the head, while keeping the involved semicircular in a plane which contains the gravity vector. This is not feasible on a table or other standard equipment. Several devices have been devised for performing 360-degree maneuvers in these planes (Furman-Pittsburgh, Li), but none that can provide complete motion control in all planes, accompanied by constant monitoring, and including ease of interpretation of semicircular canal position and nystagmus throughout.

When maneuvering the subject for testing or treatment so that the head is in various positions, it becomes difficult to maintain an envisioned orientation of the relationship of the semicircular canals to gravity. Non-electronic devices placed on the head to assist the operator directly in perceiving the orientation of certain semicircular canals, as the head is moved into different head positions, have been used, and one such device has been demonstrated by Li, but these devices have definite limitations, such as physically interfering with the maneuvers, thereby creating errors in orientation due to varying anatomy of the head, and interference with viewing the nystagmus in certain positions.

Thus, for optimum positional testing and particle repositioning strategy, it would be very advantageous to have an automated system capable of positioning subjects through 360° in all three degrees of angular freedom (pitch, roll and yaw), combined with a 3-D orientation and tracking system capable of simultaneously generating data regarding the actual orientation, relative to space and gravity, of the semicircular canals of the subject, as well as the angular acceleration being acutely imparted to the canals. Such data is preferably displayed to the operator in a form that projects pictorially the actual orientation of the semicircular canals within the subject's head to a graphical user interface GUI image of the semicircular canals. Such an image would ideally reside in a simulated environment that makes the orientation of gravity evident, as well as makes evident the routes that are available, per mechanical positioning apparatus, for the next transition to another position. Further, for optimum and simplified control of the mechanical positioning apparatus, the directionality of the controls (right hand and left hand) for transition to other positions should be made obvious.

Although the ongoing spatial orientation of the subject's head can be determined by sensors affixed to the positioning apparatus and by fixing the head thereto, it is often advantageous to fix an inertio-gravitational sensor, and/or a torque sensor, more directly to the head (such as fixed to the a head harness or to goggles). This avoids the necessity of fixing the subject's head to the chair, such restraint being uncomfortable and anxiety-producing in some subjects. It also allows testing using the neck muscles to provide the torque necessary to reach high angular velocities of the head need for certain testing.

Although, in the state-of-the-art, sensors of spatial orientation have been fixed within a virtual reality headset in combination with miniature video screens, they have not been combined with video cameras, such as infrared-sensitive cameras, so that an observer can monitor ocular movement.

BRIEF SUMMARY OF THE INVENTION

In this complex background setting, therefore, the present invention enters the scene with a remarkable and comprehensive capability to extract and acquire vestibular-related, medically informative data, and to present a simple, intuitive and clear picturing from such data of the abnormal behavioring of a very wide range of a human subject's vestibular system.

As disclosed herein in its preferred form, the system of the present invention includes: (a) an appropriate spatial maneuvering device which can be employed, either manually (i.e., either by direct hand manipulation, or by manual adjustment of a hand-operable control device, such as a joystick), or under more automated computer control, to place a subject, and in particular the head of that subject, in many different orientations in space, thus to induce vestibular activity; (b) a digital computer (or computer processor); (c) display-screen structure in an image-display zone; (d) various transducers (sensor devices, or data-stream structures) for generating electronic data-streams (referred to herein as first-category and as second-category data streams) that are supplied to, and are processable by, appropriate control algorithm structure(s) in the computer processor; and (e) one or more video cameras which are employed to view various scenes during operation of the system, and to supply what is referred to herein as camera-derived information. Also included structurally, for different purposes, and in some instances optionally, are various devices (mentioned below) that are useful for doing what is referred to herein as denormalizing, changing and selectively controlling certain perception capabilities of a subject during diagnosis and/or treatment. Sound and pressure were earlier mentioned herein in relation to denormalization. Further included if desired, are one or more subject-useable control devices (the "visual object" mentioned above) which a subject can use, on request or command, to attempt to implement certain functions, and to provide certain subjective response data as will be described below.

With regard to the mentioned spatial maneuvering device for controlling a subject's spatial orientation, this device could take on any suitable form, but for the purpose of describing herein a preferred embodiment of the invention, this device specifically takes the form of a chair which is appropriately mounted within a compound ring structure that is maneuverable angularly, and preferably under computer control, to position and move a subject's head into substantially all possible planes of orientation. This chair device can thus be employed to introduce angular motion and acceleration to a subject.

With further regard to spatial maneuvering, linear movement and acceleration can also be important. For example, in testing the otolithic organs, it is sometimes desired to alter the inertio-gravitational vector relative to the subject without evoking an accompanying cue from the semicircular canals. One way of accomplishing this is to provide gross linear oscillation to the subject. This can be accomplished, as an illustration, with a linear track on which a subject-supporting chair unit travels on rollers or wheels to move the subject in a linear, oscillating manner. An important advantage of the present system for linear-oscillation testing is that a subject can be positioned through 360-degrees in any angle of the roll, yaw or pitch planes of the subject relative to the linear track and the direction of oscillation, thus providing a manner to test the otolithic organ through any plane of its functionality. State-of-the-art devices do not provide this capability. Combinations of other inputs described herein can be simultaneously applied during these linear oscillation tests, another capability not provided by state-of-the-art devices.

Other linear motion procedures may also be performed, and all such procedures can be practiced in accordance with the enhancement the capabilities of the present invention.

Thus, in broad terms, practice of the present invention in relation to investigation and diagnosis involves inducing vestibular activity in a subject by selectively orienting (positioning) that subject in different spatial dispositions, and by then collecting both absolute positional data (preferably from several sources, and referred to herein as first-category data relating to patterns and conditions of subject orientation), and subject-vestibular-response data relating to these dispositions (referred to herein as second-category data associated with patterns and conditions of a subject's outwardly expressed behavior which is linked to vestibular activity). Such data is employed variously to generate (create) an easily viewed, pictorial, sophisticated visual correlation (or correlations) between certain components of the data, which correlation(s) play(s) an important role in informing the attending physician (or other party) about any problematic characteristics of the induced vestibular activity.

From the treatment and/or rehabilitation point of view, once a diagnosis has been achieved, the system computer, in a preferred manner of practicing the invention, can be instructed to execute one or a series of spatial-orientation maneuver(s) (linear and/or angular) to urge correction, etc.

of the detected source problem. Manual maneuvering (by either of the "manual" methods generally mentioned above) could also be employed on the basis of diagnostic information, especially as aided by guiding information given by, and as a result of, precision computer processing.

DETAILED DESCRIPTION OF THE INVENTION

What follows now is a detailed description of a preferred embodiment of the invention, made with reference to the four drawing figures, and blended with commentary relating to various alternatives and modifications that can be made within the practice and concept of the invention. Also presented are certain operational examination and treatment opportunities and advantages which are made available by the system and method of the invention.

Figure 1:
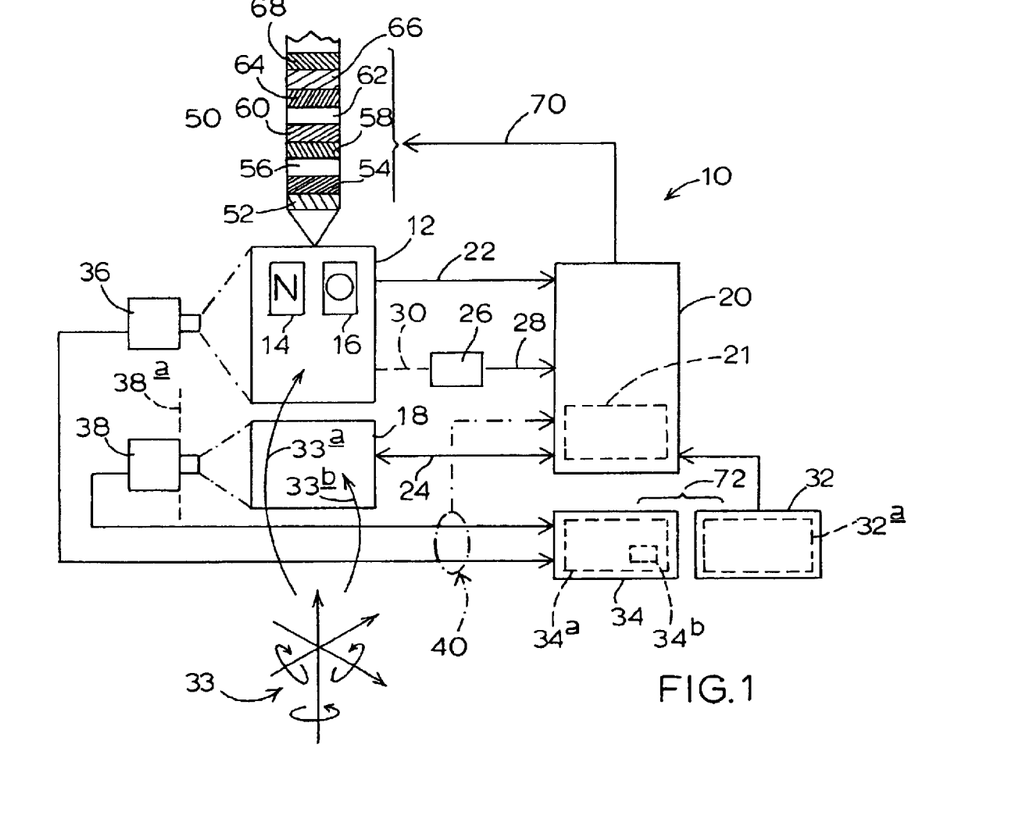
FIG. 1 is a block\schematic diagram showing a preferred embodiment and manner of practicing the invention.
Figure 2:
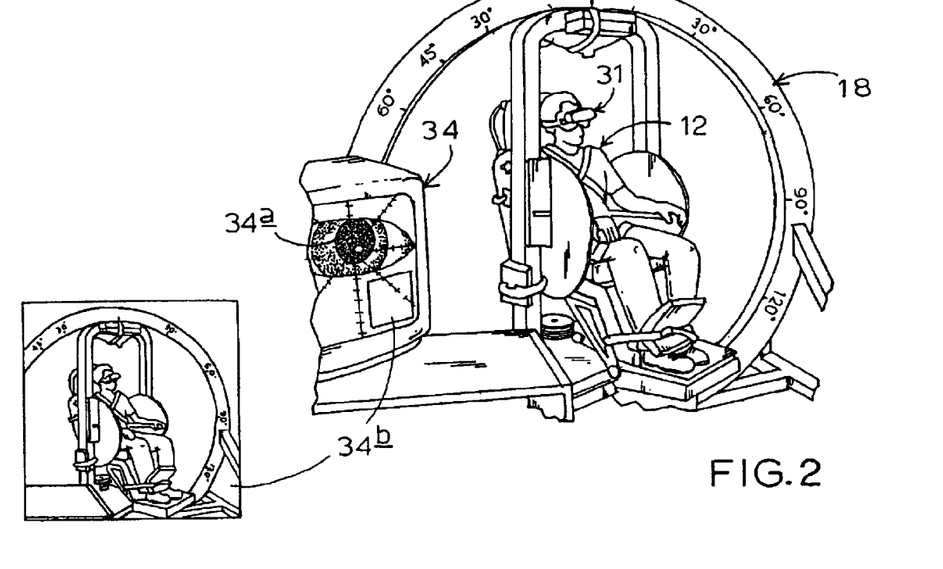
FIGS. 2 and 3 are photographic drawings picturing a human subject supported in two different angular orientations in a chair which is part of one form of a spatial maneuvering and positioning device employed in and by the invention system and methodology illustrated in FIG. 1. These two figures also each show a video display screen which is illustrated presenting a correlated, two-picture-in-picture image field, wherein one picture shows a general video overview of the maneuvering device and supported subject (the small picture), and the other, larger picture shows a video close-up of one of the subject's eyes.
Figure 3:
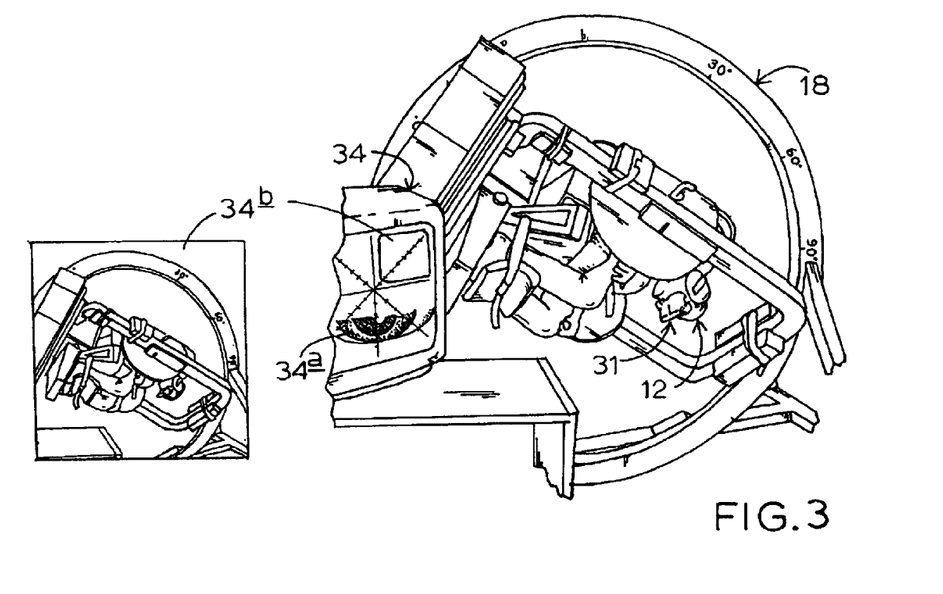

With reference first, therefore, to FIGS. 1, 2 and 3, indicated generally at 10 in FIG. 1 is a system constructed as a preferred embodiment in accordance with the present invention. As pictured in FIG. 1, the entirety of system 10 is illustrated in block/schematic form, inasmuch as particular details of structure do not form parts of the present invention. Further, as illustrated in FIG. 1, system 10 is shown there in a condition poised to practice the invention in conjunction with a human subject who is represented simply in block form at 12. Shown within block 12 are two smaller blocks 14, 16, labeled with the capital letters "N" "O", respectively. These blocks collectively represent portions of the subject's vestibular system, and specifically those components which relate to vestibular activity. Block 14 relates to nystagmus activity which is sourced by the subject's angular acceleration sensors—the semi-circular canals. Block 16 relates to otolithic-organ activity which is sourced by the subject's linear acceleration sensors that, among other things, are principally responsible for gravitational perception.

In system 10, subject 12 is appropriately fastened and stabilized with respect, to a spatial orientation maneuvering device shown by block 18. This device can take any one of a number of different forms. For example, it can be designed as a purely single-axis, dual-axis, or triple (orthogonal) axis angular-motion machine. Such a machine is specifically illustrated and described herein with reference to a preferred embodiment of, and manner of practicing, the invention. It can be a linear motion machine. It can be completely open all around, or it may be formed in part as, for example, a geodesic sphere, or partial sphere, new blocking or otherwise. It can accomplish subject positioning and movement under computer-implemented motor control, or completely manually. Its maneuvering motions can be motor-driven directly by commands from subject "occupant" who is, for example, instructed what to do. And, it can be computer programmed to perform very specific pre-determined maneuvering patterns. There are, of course, many other possibilities.

Preferably, and for the purpose of illustration herein, device 18 takes a form like that which is pictured in FIGS. 2 and 3, and namely, the form of a subject-support chair which is mounted within plural, articulated, motor-driven ring structure which can be operated, either under manual direction, or under computer control, essentially to position subject 12 in substantially any plane of interest, and specifically with the subject's head oriented in any plane of choice. FIG. 2 shows device 18 orienting a subject in one upright orientation, and FIG. 3 shows the same subject in a rotated and somewhat inverted different orientation.

While device 18, in the form which is shown in FIGS. 2 and 3, essentially can maneuver the subject rotationally with respect to the three orthogonal axes which are normally thought of as representing spatial dimensions, it is entirely possible that this device might only be capable of orienting the patient about lesser number of axes, if a three-axis device is not available. In the case of maneuvering being performed with equipment which offers less than three-axis adjustability, practice of the invention is still fully enabled, taking into account that actual spatial-orientation maneuvering of a subject will be performed differently—and even simply manually on a surface, such as on a table surface.

Appropriate regions in device 18 are equipped with gravitational and rotational accelerometers which supply data-streams indicative of the exact orientations which the device "thinks" describe a subject's disposition in space. Data in these data streams will always accurately report on the condition of the device, but not necessarily on the absolute spatial orientation of a subject's head, unless, of course, the subject's head is "bound" to the device via suitable restraints.

For important safety reasons system 10 includes an appropriate cut-off foot switch that stops all positioning activity when released, a microphone for constant communication with the patient and, in case of power failure, the ability to return the chair manually to upright and disembark the subject.

Also included in system 10, is an appropriate algorithm-equipped digital computer 20 which is illustrated effectively interconnected with subject 12 and device 18 through two connection lines, or paths, shown generally at 22, 24, and also through a block 26 which, as will shortly be explained, constitutes a subject-available control device, or devices, connected to computer 20 through a line shown at 28, and made available for control by a subject, such as subject 12, through what is shown in FIG. 1 as a dashed line 30). Appropriate vestibular analysis and processing algorithm(s) is (are) shown by dashed block 21 in computer 20. While details of such algorithms do not form any part of the present invention, certain considerations which relate to specific algorithm design will become apparent to those appropriately skilled in the art as the description of the invention continues herein. Block 26 specifically represents what was referred to earlier herein with the term "visual object", and it can be singular or plural in nature. More will be said about such an object later herein, but it is worth noting here that it is through such an object that a subject-response data-stream (voluntary) can be taken into account.

Line 22 which extends visually in FIG. 1 from subject 12 to computer 20 represents a data-flow line through which various kinds of subject-specific data is fed to the computer. For example, in the system arrangement and setup now being described, subject 12 is specifically equipped with attached headgear (see goggles 31 in FIGS. 2 and 3) which includes, in accordance with the invention, appropriate accelerometers (not specifically illustrated) that are designed to feed spatial-orientation and angular-disposition and motion data to the computer. Line 22 may also be employed to feed other data to computer 20, through appropriate channels contained within the "line", and these other channels might carry, for example, other subject-specific data which might relate, for example, to various perception and environmental controls and/or stimuli that may be placed on and created for the subject during vestibular examination and/or treatment. Such controls and stimuli will be discussed shortly herein.

Line 24 in FIG. 1 includes channels that may be employed with respect to appropriate accelerometers (not specifically shown) provided on device 18 per se to communicate to computer 20 the actual spatial orientation and position which device 18 is then nominally establishing for subject 12. Other appropriate data may also be communicated by this "line" to the computer, such as angular-motion data, speed-of-motion data, acceleration and deceleration data, etc. Further, appropriate channels in line 24 may be employed by computer 20, as indicated by the line's left-pointing arrowhead, to drive and control the motor-drive componentry appropriately provided in device 18, thus to place angular and spatial positioning (orienting) of subject 12 more completely under the direct control of computer 20.

The small graphic symbols which appear at 33 at the bottom of FIG. 1 represent the three, orthogonal, usually referred-to spatial axes, with associated rotational vectors pictured curling around these three axes. Extending upwardly from this graphic symbol are two, long, curved arrows, one of which (32a) points to subject 12, and the other of which (32b) points to device 18. Collectively, this symbolic imagery has been placed in FIG. 1 to emphasize the fact that both device 18 and subject 12, during a typical procedure involving this subject, undergo spatial and angular position adjustment. While the subject is nominally "fastened" to the chair, there is nonetheless a certain amount of important orientation differentiation which may take place, especially where the subject's head is not tightly bound to the maneuvering device's structure. Experience indicates that many people are reluctant to be so head-bound, and this is a reason why, preferably, the system of the invention is employed with a subject's head equipped with appropriate accelerometer-bearing headgear so that actual spatial orientation of a subject's head can be noted independently.

Further included in system 10, as pictured herein, are two screen display devices shown at 32, 34. Device 32 is directly connected to computer 20, and device 34 is connected to receive signals, as shown in FIG. 1, from two different video cameras which are illustrated at 36, 38. Optionally, and as is indicated generally by dash-dot lines at 40 in FIG. 1, video information from cameras 36, 38 may also be provided directly to computer 20. What is pictured according to the invention on display screen 32, directly from computer 20, will be discussed shortly hereinbelow. What is presented on the display screen in device 34 (see especially FIGS. 2 and 3) preferably constitutes a composite (such as a picture-in-picture-composite) of the points of view established respectively by cameras 36, 38.

Camera 36 is, according to the invention, a very small infrared video camera (or in some instances two small video cameras—one for each eye), directed at the eye(s), and installed within subject-wearable, light-occluding goggles, such as the goggles and headgear which are pictured at 31 on the subject shown in FIGS. 2 and 3. Such a tiny camera, or cameras, look(s) appropriately at one or both of a subject's eye's during operation of system 10, thus to enable a display on the screen in device 34 which clearly shows subject eye condition (position, movement, and direction of movement) as a strong visual aid in observing nystagmus activity. The image of a single eye of subject 12 is shown at 34a in FIGS. 2 and 3. In most instances, only one eye needs to be monitored.

With such a goggle arrangement, responses in the form of the subject's eye movement are detected in a light-excluding environment in order to minimize suppression of nystagmus by optic fixation. These responses are analyzed electronically by computer 20 to note and record the axis of rotation, angular velocity and direction of each movement. Camera 38 preferably is a singular camera which views the entire scene of a subject, such as subject 12, and a maneuvering device, such as device 18, so as to present on the screen in display device 34 a visual image of the actual orientation of the subject as a whole in space during an observation and/or treatment procedure. Such an overall view is shown generally as a small picture-in-picture component 34b on the display screen in device 34 as such is shown in FIGS. 2 and 3.

Associated with camera 38, as such is pictured in FIG. 1, is an upright dashed line 38a. Line 38a is included in FIG. 1 to represent and symbolize schematically a modified kind of installation for camera 38, whereby the camera may be mounted on a conventional track and dolly system that allows the point of view of the camera to be shifted multidirectionally in the area around maneuvering device 18.

Thus, and still referring especially to FIGS. 2 and 3, one will see how, on the display screen in device 34, the attending physician, or other party conducting an examination or treatment can in a single glance at this screen observe the actual three-dimensional position of the subject as a whole in space, along with the condition of eye activity of the subject at the same moment in time. As was mentioned earlier, the optional connection from camera 36, 38 to computer 20, represented by dash-dot lines 40 in FIG. 1, can feed all video-camera information directly to the computer which can employ it, along with other information still to be discussed, also in a display presented on the screen in display device 32. A displaying on the screen in device 32 is shown generally in dashed lines at 32a in FIG. 1.

Returning for moment to the interconnection 26, 28, 30 which is shown extending generally between subject 12 and device 18, as was mentioned earlier, block 26 in this interconnection represents one or more subject actuateable control devices, such as (a) a joy stick, (b) a lever, (c) one or more push buttons, (d) a computer mouse, or (e) another device which the subject can, either voluntarily or on command or request, use to enter information regarding subjective response to something which is taking place, or which is being experienced by the subject, during an examination and/or treatment procedure. For example, in a gravi-perception test the subject might be asked by the attending physician or other party to enter some information via an appropriate control device to indicate the subject's then perception of the direction of gravity. This data, along with computer "knowledge" of actual subject orientation as derived from sensors applied to device 18, and from sensors, if any, contained in subject headgear, can be used by computer 20 to ascertain something about the subject's then vestibular activity as that activity.

Finishing now a description of what is shown in FIG. 1, indicated generally at 50 is a broad, downwardly pointing arrow which touches block 12 that represents the mentioned subject. Plural, differently shaded (or non-shaded) horizontal bands are pictured in this arrow to symbolize and represent respectively different environmental and/or perception stimuli that may be applied to a subject, one or more at a time. Such stimuli are employed, inter alia, effectively to denomalize one or more of the subject's perception capabilities. Such denormalization according to practice of the invention aids in testing, observing and treating abnormal vestibular activity by applying certain controls which will help to expose and identify sources of abnormal vestibular behavior.

Arrow 50 has its upper end fragmented in order to stress the point that there are many different specific denormalization, etc. protocols which can be applied, and several of them, for illustration purposes, are specifically mentioned herein. Thus, shown in arrow 50 are nine representative horizontal bands 52, 54, 56, 58, 60, 62, 64, 66, 68. These bands herein represent, respectively, the following different denormalization conditions: light occluding goggles (52); controlled virtual field of view (surroundings), as, for example, can be created on a suitably spaced and positioned image-bearing surface expanse (screen) (54); controlled virtual or real (spatial) three-dimensional images (56); sound alteration (58); ear pressure alteration (60); inner ear temperature (caloric) alteration (62); voltage application to the head (64); head vibration (66); and angular and/or linear acceleration and motion (68). Each of these several denormalizing stimuli, or applicators of stimuli, can be introduced independently or interdependently, either manually, or, in certain instances, under computer control, as is suggested by control line 70 pictured in FIG. 1.

Figure 4:
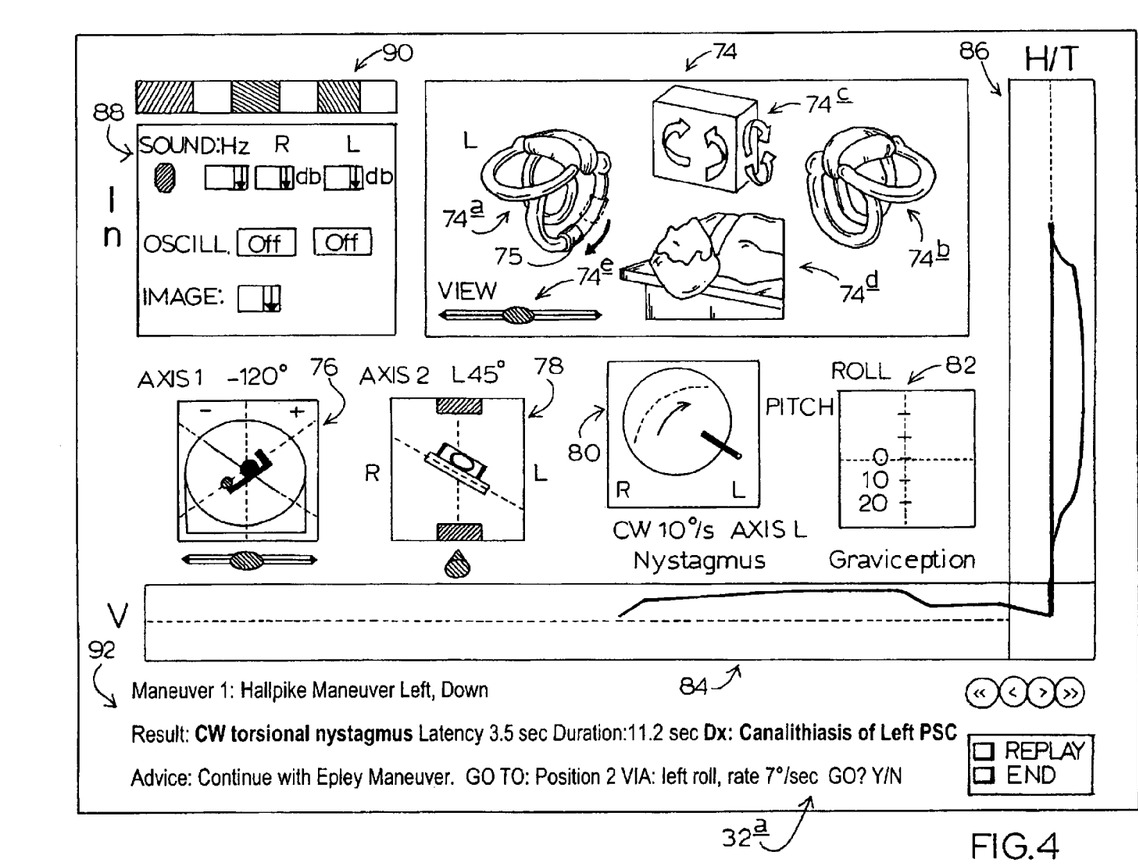
FIG. 4 shows a computer monitor display screen which is seen presenting a large plurality of correlated graphic and pictorial images, some of which function, according to the invention, as user-interactive control icons.

Completing now a description of the system structure and methodology pictured in the several drawings figures, and looking now particularly at FIGS. 1 and 4, a bracket designated 72 in FIG. 1 represents a "gathering" of display devices 32, 34 into what is referred to herein as an image display-zone, wherein pictorial, and other, graphic information, soon to be more fully described, is presented on the display screens in devices 32, 34. Such graphic information is thus collected essentially at one location for easy, single-point-of-view viewing by the physician or other operator using system 10. Such gathering, accordingly, uniquely places before that operator the opportunity to view a large collection of interrelated, and dynamically changing, gathered data, which relates to a particular investigation and/or treatment procedure that is underway.

It should further be noted that, while in the specific illustration of system 10 presented herein two separate display devices, 32, 34 are shown and described, it is entirely possible that all visual display material could be presented on a single display screen, such as the display screen shown generally by dashed line 32a in FIG. 1, which represents the display screen in display device 32. Under such a circumstance, the alternative connection represented by dash-dot lines 40 in FIG. 1 would be active to feed to computer 20 video data collected from the various video cameras employed in the system, such as cameras 36, 38.

The importance of gathering and presenting in visual form a wide range of operative subject and systemic data at essentially at a single viewing location herein plays an important role in creating advantage which is offered by the present system and methodology. This advantage includes the fact that this system and methodology essentially collect at a common site a huge quantity of dynamic information that can quickly inform a system operator about observable vestibular activity taking place in subject 12 during a procedure.

One possible and very useful display of information in graphical and pictorial form that can be presented is shown on display screen 32a as pictured in FIG. 4. Here in FIG. 4 there are, generally speaking, nine different pictured graphical pictorial image areas which are shown generally at 74, 76, 78, 80, 82, 84, 86, 88, 90. A text-presentation area 92 is also provided within the area of screen 32a shown in FIG. 4. While these several specific image site areas have been chosen for illustration herein, it should be appreciated, and it will become apparent, that a greater or lesser number of site areas, and the specific internal contents of each such site area, can be changed and varied within the scope of the invention, and specifically to suit different specific system designs and applications. No matter what in fact are the contents presented on display screen 32a, at the least, these contents include an appropriate presentation to a user of system 10 of intuitively and easily grasped visual and pictorial information that correlates different components of data that are presented and gathered by computer 20 during an investigation and/or treatment procedure.

Very specifically, it is a feature of the present invention to provide such visually correlative data which will give a system user an intuitive and quick grasp of the specific vestibular behavioral situation which is underway in real time, and at any given moment, with respect to a subject whose vestibular system is being explored and/or treated. Contents which are pictured as being displayed on screen 32a in FIG. 4 demonstrate this important capability and offering of the present system.

Included within image site area 74, are five pictorial/abstract icon-like images 74a, 74b, 74c, 74d, 74e which represent different things, as will now be described. Each of these images takes the form herein preferably of a user-accessible interactive control icon which will allow a user, through manipulation of a control device, such as a mouse, and the cursor driven by the mouse, to perform various manipulations of the spatial orientation of subject 12 in system 10. Icons 74a, 74b, are pictorial, virtual, surrogate, anatomical representatives of the right-side and left-side semi-circular canal structures, respectively, in subject 12, positioned relative to one another, and pictured with a spatial orientation which is intended to match very closely the actual orientations in space of the subject's actual semi-circular canal structures. The icon images which are presented at 74a, 74b are rendered with appropriate three-dimensional cues on a two-dimensional screen, whereby they quickly give a viewer a clear understanding of the orientations and dispositions of these canal structures.

By placing, for example, a mouse-controlled cursor on either one of these representative icons, and by maneuvering the cursor through appropriate mouse manipulation, the system user can call for a fairly exact repositioning at any time of an actual canal structure in the subject. Such manipulation will result in a control signal being sent by computer 20 to the motors that control operation of device 18, so as to orient the subject, whereby the accelerometers that are responsive to the subject's head position directly produce an indication that the subject's head has been repositioned. The data-streams which control the spatial representations of icon images 74a, 74b on screen 32a come to the computer from the headgear accelerometers via communication line 22 as shown in FIG. 1. This collection of data essentially represents what might be thought of as absolute three-dimensional spatial-orientation data regarding the then subject's head position and orientation.

A small visual element, shown in image site 74 at 75, is appropriately creatable under computer control to represent the positions and flows of various particles and activities which may be playing a role in a vestibular problem that is being experienced by the subject. Under appropriate commands, not specifically illustrated herein, a system user can call for the presentation of this small visual element, with positioning of the element along the run, for example, of a given semicircular canal, being determined through computer calculation based at least in part upon data coming from the headgear accelerometers, and other data components that are received during a test and/or treatment procedure. The exact manner of creating such a small visual element and placing it appropriately along one of the canals is completely a matter of user and system-designer choice, and can be implemented in a number of different ways, none of which forms any special part of the present invention. Further, algorithmic information contained within computer 20 which permits representation and control through icon visual elements 74a, 74b is well within the skill levels of those generally skilled in the art of writing computer programs, and is not considered to be any part of the present invention. Suffice it to say that there are many different approaches which one can use to implement such moveable and control iconry.

Visual icon elements 74c, 74d relate in slightly different ways to the actual orientation in space of the elements in manipulation structure 18. Both, of course, are virtual representations, with icon 74c being quite abstract in nature and icon 74d being somewhat pictorially representative of a subject within the chair in device 18 as pictured herein. Both of these icons are user-interactive icons which can be manipulated through mouse and cursor control to effect re-positioning, and appropriate rotational positional motion, of the interconnected structures in device 18. These icon elements appear to, rotate within image site 74 when structure within device 18 moves from one condition to another. A user, by manipulating either one of these two icons through mouse and cursor control, can thus cause the computer to send appropriate control signals to operate the motors in device 18. The actual spatial conditions which are thus achieved and represented by the positions of the icons on screen 32a are synchronized through one or more datastreams received by computer 20 over communication line 22 from appropriate accelerometers directly attached to components in the maneuvering device.

Icon component 74e is a virtual representation of a control slider which, as pictured in FIG. 4, is permitted generally horizontal adjustment to the left and to the right under mouse and cursor control, to shift the point of view, for example, of a camera structure such as camera 318. Appropriate manipulation of the slider knob in this icon to the left and to the right will cause the surrogate pictorial representation of a subject in the maneuvering device chair to rotate within image site 74 so as to reflect a selected new point of view.

It should be understood that, no matter whether a position and spatial orientation adjustment occurs through manipulation of the icon components within image site 74a, any motion and repositioning taking place with respect to the components in device 18, and with respect to the actual orientation of the head of subject 12, will be communicated through computer 20 to the representations of the respective iconry within image site 74. In other words, these icon images will follow whatever positional adjustments and establishments take place.

It will thus be apparent that, simply by observing what is seen within image site 74 on display screen 32a, the system user receives immediate correlative data that relates the actual spatial condition of the maneuvering device with the actual spatial condition of the subject's head, and thus of the subject's two semi-circular canal structures.

Image sites 76, 78 contain appropriate iconry which represents two different axial point of views relating to motion or rotation axes that are furnished within maneuvering device 18. Image site 76 pictures a side view, so-to-speak, and image site 78 a top axial view. A slider control which is included at the base of image site 76, and a rotary virtual knob control which appears at the base of image site 78, is/are manipulatable through mouse and cursor control by a user, and through the agency of operation of computer 20, directly to manipulate maneuvering device chair motion in selected angular manners. The specific central icon imagery which is presented at these two sites adjusts in pictorial condition to reflect actual conditions, and thus to reflect motion between one condition and another condition of, for example, the chair that supports subject 12. Numeric reports with respect to angular disposition about different axes can readily be provided in association with these image sites, and such information is generally pictured numerically at the upper sides of image sites 76, 78 in FIG. 4.

Manipulation of the chair structure through controls provided via iconry in sites 76. 78 will be reflected by imagery positional changes of the icons that are associated with such conditions as pictured in image site 74.

One of the appropriate algorithmic components of the algorithm structure contained within computer 20 observes various data components supplied to the computer, such as motion components supplied directly from visual imagery obtained through camera 36, to assess current nystagmus activity in one or both of a subject's eyes. This activity, which can be thought of as being involuntary subject activity, and which can depend, in certain instances, upon the spatial orientation, upon the angular motion or acceleration, and/or upon various disease processes, of and relating to subject 12, is processed by the computer, and presented in graphical and visual form within image site 80 in FIG. 4.

Image site 80 depicts the momentary profile of the fast phase of the ongoing nystagmus, as determined by either digital nystagmus analysis or input from the observer. Inasmuch as any movement of the eyeball during a moment in time involves a rotation in a certain plane, and thus about a certain axis that is perpendicular to that plane, it is possible to depict any such movement by designating the coordinates of the axis and the direction of angular movement about that axis. Thus, the sphere (the circle) depicted in site 80 represents the eyeball as viewed from the frontal plane, the projecting pole represents an axis, and the curved dashed line represents the plane of rotation of the equator. The curved arrow points out the direction of rotation about the mentioned axis.

With what is shown in image site 80 presented along with what are shown in image sites 74, 76, 78 herein, it will be very apparent how the system and methodology of this invention present, graphically and visually to an observer, intuitive and easily graspable correlative data that links actual spatial orientation of a subject and of a subject's head to a subject's involuntarily created condition of nystagmus activity. This correlative-data presentation provides a powerful tool in real time for a user of the system to gather and form an assessment regarding the efficacy of treatment, if that is what is taking place, and/or to reach a diagnosis relating to vestibular problematic behavior.

Image site 82 relates to another subjective data stream, but here one which is created voluntarily on invitation or command from the system user directed to the subject to introduce an input, for example, which reflects the subject's perception of the gravitational vector. This kind of information, for example, can be supplied to the computer in system 10 through control block 26 pictured in FIG. 1.

The system will, of course, "know" quite absolutely what in fact is the subject's gravitational orientation, as derived from the accelerometers mentioned hereinabove, and also what the subject's own perception of the location and direction the gravitational vector is, as introduced through control block 26. These two categories of data are presented by computer 20 in a comparative sense on and within the image presented at image site 82 in FIG. 4. Here, therefore, a user of the system can observe immediately another content of correlative data which relates absolute orientation in space relative to the gravitational vector to subjective voluntary input data. A difference existing between these two reflections of the orientation of gravity will give the system user an immediate intuitive grasp of the nature of a vestibular problem being experienced by the subject with respect, for example, to the dysfunction of the otolithic organs, and/or perhaps also by dysfunction in one or more of the semi-circular canals.

Recognizing now the presence in the screen display presented in FIG. 4 of such a rich supply of spatial orientation and subject perception (both voluntary and involuntary) regarding various components of vestibular activity, it should be very apparent how the system presents to a user an extensive and quite easily grasped all-over "image" of the behavior of the subject's vestibular system, as such behavior is dictated by specific orientations in space, and/or by specific motions in space between different orientations. The two, divergent time-based curves or graphs which are represented in image areas 84, 86 display the recent nystagmus slow phase velocity data in a scrolling manner that allows for improved review and analysis through a greater insight into the present and previous responses. This can be provided by virtue of a divergent scrolling design that is highly intuitive as follows: first, the deflections of the horizontal and vertical tracings of eye movement are converted into their respective slow phase velocity components; second, the intensity of these components is indicted by the extent of their deviation from the median line of the graph; third, the direction of their deviation is determined by the actual direction of the fast phase of the nystagmus, which is the direction by which nystagmus direction is conventionally indicated; and fourth, these tracings are oriented to scroll in two diverging directions—horizontally from right to left, and vertically upward. Tracings scrolling along the horizontal line represent the vertical component of the slow phase, so that its deflections will be vertically oriented, and an upward deflection represents an upward-directed slow phase, and vice versa. Tracings scrolling along the vertical line represent the horizontal component of the slow phase, so that its deflections will be horizontally oriented, and a rightward deflection represents an rightward-directed slow phase, and vice versa. Finally, this scrolling keeps its origin point at one general location, but the resultant tracing continues to scroll horizontally across or vertically up the page, so that the time line of recent activity will become apparent. A cursor across the median line of each graph can be moved to a particular point and a cursor on the other graph will be automatically moved to the same point in time. The operator can thus move to a previous point in time to review a particular sequence, with the remainder on the graphic display playing out the sequence.

In other state-of-the-art software displays of nystagmus, the tracings of both vertical and horizontal components course horizontally across the screen, making interpretation less intuitive.

In addition, the present design can provide for the slow phase velocity of the torsional component to be displayed with the horizontal channel tracing, but in a different color, denoting the left or right angular direction of the superior pole of the fast phase.

Actual angular acceleration data from the angular acceleration sensors can also be depicted in the display, placed as a separate tracing (distinguished by color or character, in virtual real-time adjacent to the slow-phase velocity (SPV) tracing, and oriented in their respective vertical and horizontal channels of the SPV display. Thus, the expected normal positioning-induced nystagmus, and after-nystagmus, from angular acceleration of the head can be correlated with the actual nystagmus tracing, and will be less likely confused with particle-induced nystagmus. Also, the timing, direction and velocity of transition and test moves will be more evident.

As was mentioned above, there are many instances in which observation and exploration of vestibular behavior is best detected under circumstances where one or more of the normal perception capabilities of a subject, such as subject 12, are in some fashion denormalized. Several different characters of denormalization have been specifically mentioned, and implementation of these different forms of denormalization is represented in FIG. 1 within the horizontal numbered bands that are pictured in arrow 50 in FIG. 1.

Operation and use of the present invention does not necessarily depend upon the presence or absence of any one or more of these denormalization protocols, but the method and system of the invention are embrasive in certain instances of use of one or more denormalization protocols, in order to enrich the quality of exploration and treatment made possible by the system and method of this invention.

With regard to any specific denormalization protocol, such as, for example, the occluding of normal vision by the installation of light-occluding goggles, such a protocol can be placed under the appropriate control of computer 20, if so desired. Data that is relevant to such denormalization can be derived from appropriate sensors that detect the presence of a denormalization protocol, and perhaps in some instances on the, supply of data relative to certain characteristics of denormalization.

In FIG. 4, the image area marked 88 is presented as an illustration of how one of the mentioned forms of perception denormalization, and namely one involving the introduction of sound to one or more of the users ears through appropriate ear phones, can be viewed and controlled, and observed by computer 20. Thus, within image area 88 in FIG. 4, one can see that there are controls provided relative to sound denormalization involving selection under computer control of the frequency content of introduced sound, and of the relative volumes of this sound denormalization activity as presented to the left and right ears in a subject. Various on and off controls are provided to afford flexibility in sound application, and with a protocol being employed, and with information thus presented on display screen 32a, the system thus now presents to a user not only all of the intuitive correlative data that has been described earlier with respect to the other image areas presented in FIG. 4, but also a rich supply of data describing real-time denormalization parameters, so that a user of the system can quickly grasp how such denormalization activities affect vestibular behavior.

While sound presentation is specifically illustrated and described with respect to what is shown in FIG. 4, it will be apparent to those skilled in the art how different, other ones of the mentioned denormalization protocols can similarly be placed under computer control, and observed in a visual fashion within the content of a unified display screen such as that shown in FIG. 4.

Image area 90 represents the option of equipping system 10 with appropriate user interaction controls through the imagery on screen 32a to call up specific spatial orientation conditions and/or motions that may be especially useful to a particular treatment and/or examination underway. The various shaded and unshaded divided areas within the long horizontal bar which is image area 90 in FIG. 4 represent different such selectable positions and/or motions. The exact number of such selectable conditions is entirely a matter of user and/or system designer choice, and specific selectable motions and/or spatial orientations can be fully preprogrammed and set for specific known useful conditions, and/or can be completely programmable under user control, and through employment of computer 20.

General Commentary Regarding Structure and Methodology

The following text generally visits various structural and operating features and potential modifications relating to the invention. It offers a wide-ranging exposure regarding the scope and flexible utility of the invention.

In the display shown in FIG. 4, the virtual three-dimensional model of the semicircular canals, oriented to indicate the real time orientation in space of the subject's semicircular canals, and their cupulae, is displayed in a highly understandable form at the graphical user interface, at the operator workstation. For instance, each canal may be color-coded, or the operator may desire to observe the position of only certain SC's with other excluded or translucent. This display greatly assists the operator to understand the ongoing relationship of the SCC's to gravity, and to assist in the repositioning process. This display in generated by simultaneously interfacing the nystagmus analyzer information with the SCC orientation data. When nystagmus is elicited by position or positioning, and is perceived by the system to be a form that is most likely to be generated in the SCC's, the most likely generating SCC can be highlighted or marked in some way (e.g. showing particles descending through the canal), and the other SC's can become less marked, or more transparent, in order to allow ease of observation of the offending canal. The apparent, real time, position of the particles within the SC or at the cupula can be indicated on the virtual model, taken from a combination of chair position and the elicited nystagmus. Also, the operator can have the option of zooming in when needed, as for a better view of the cupular or particular relationship. The operator can undertake both diagnosis and treatment, monitoring the ongoing orientation in space of the SC's and the probable relationship of the particles at all times.

Thus, the graphical user interface displays the inputs (stimuli), active or inactive, to the subject, including sound to either ear, pressure to either ear canal, head oscillation, visual images and positioning; as well as the subject's responses, after varying degrees of computer analysis to make them more understandable, including graphical analysis of the slow phase velocity of the on-going nystagmus, slow phase velocity of the nystagmus in the vertical, horizontal and torsional planes, graphical semicircular canal orientation, and a graphical schematic model of the instantaneous head position. Associated with this graphical schematic model of the instantaneous head position is a graphical depiction of the available planes, and clearly identified controls for accessing them, through which the operator can actuate the positioning mechanism for maneuvering the subject to other positions. There are also various simulated controls by which the operator can actuate the input stimuli, position the subject and respond to ongoing queries of the intrinsic software. This is accomplished by the design of the graphic user interface.

The operator can have the option of motion control of the positioning mechanism more or less directly, or using the computer display for orientation and control, or by deferring to the inherent computer control. For the latter, the operator can select from a list of standard positions and transition routes, as by placing the mouse on the written or icon selection, which the computer will thereupon undertake. Optionally, the operator can select the moves recommended by the inherent expert system.

The virtual three-dimensional model of the instantaneous spatial orientation of the head and/or body, and the graphical depiction of the momentarily available planes of angular rotation through which the operator can actuate the positioning mechanism, as well as clearly identified controls for accessing them, is advantageous, because the operator will, at any point in time, only have at his disposal for accomplishing the next move the angular motion through those planes provided by virtue of the inherent design of the positioning mechanism. In addition, as the subject is maneuvered through different positions, the directional orientation of the available planes of angular freedom is constantly changing and may in fact become reversed. These factors lead easily to confusion for any but a highly skilled and experienced operator. Thus, one purpose of the invention is to simplify this task so that a relatively unskilled or occasional operator can easily carry it out.

This simplification can be accomplished by pictorial structure, including virtual three-dimensional imagery, that provides an intuitive sense of the momentary spatial relationships of the subject, the semicircular canals and the motion control directionality.

Also, the virtual viewpoint for observing the changing spatial orientation of the canals, nystagmus, etc., can, through adjustment of the operator interface display, be either off board (earth-fixed, with the subject changing position) or onboard (head-fixed, with the environment changing position), with either option to be selected by the operator. Means can also be provided for the operator to select different virtual viewing orientations whether off board (in relation to the positioning apparatus) or on board (in relation to the head and semicircular canals).

In addition to the virtually instantaneous output data, the graphical user interface can display the recent nystagmus slow phase velocity data in a, scrolling manner that allows for improved review and analysis through a greater insight into the present and previous responses. This can be provided by virtue of a divergent scrolling design that is highly intuitive in that the deflections of the tracings of the horizontal and vertical slow-phase velocity (SPV) components move in the actual direction of the fast phase of the nystagmus, which is the direction by which nystagmus direction is conventionally indicated. Thus, the tracing of the horizontal component scrolling vertically upward provides a leftward deflection to depict a leftward direction of the nystagmus fast phase, and vice versa. Likewise, the vertical channel coursing horizontally, scrolling from right to left, provides an upward deflection to depict an upward direction of the nystagmus fast phase, and vice versa. In other state-of-the-art software displays of nystagmus, the tracings of both vertical and horizontal components course horizontally across the screen, making interpretation less intuitive.

In addition, the present design can provide for the slow phase velocity of the torsional component to be displayed with the horizontal channel tracing, but in a different color, denoting the left or right angular direction of the superior pole of the fast phase.

Actual angular acceleration data from the angular acceleration sensors can also be depicted in the display, placed as a separate tracing in virtual real-time adjacent to the SPV tracing, and oriented in their respective vertical and horizontal channels of the SPV display. Thus, the expected normal positioning-induced nystagmus, and post-rotation nystagmus, from angular acceleration of the head can be correlated with the actual nystagmus tracing, and will be less likely confused with particle-induced nystagmus. Also, the timing, direction and velocity of transition and test moves will be evident.

Consistent with the overall intuitive plan of the design of the graphical user interface, there is consistent orientation of all left-right objects and indicators. In addition, the operator can select the option of having "screen-left" oriented to the user's right, or vice versa. The former configuration is the more universally desired because the nystagmus, as viewed face-on, places the subject's left to the user's right.

The intrinsic software may formulate and advise various optional levels of treatment recommendations (e.g. conservative, aggressive or extrinsic to the system.) From this, the operator can, when indicated, undertake treatment of the subject either directly by manual control of the system, or indirectly by computerized control of the system, using such modalities of treatment as maneuvering the subject's head into various positions relative to gravity, or moving the head through various planes, as is indicated according to both well-known and novel procedures for repositioning of free, adherent or jammed intracanalicular masses. Other test/treatment modalities include the application to the head of oscillation or acceleration-deceleration, the presentation of a visual image and the presentation to the ears of sound, or pressure via an onboard headset.

The operator may interface with the system through monitors, a keyboard, touch-screen, cursor or similar device, including special controls (e.g. joystick, track-ball, mouse or switches) that actuate, move or control parts of the system.

In addition, the graphic user interface can display the subject's subjective responses such as graviception (the perception of gravitational direction), showing both roll plane and pitch plane orientation of the subject's graviception indicator object. The orientation of the positioning chair can also be depicted.

The system may carry out ongoing monitoring during treatment procedures (e.g. canalith repositioning maneuvers), and the intrinsic software may recommend or undertake, based on the real-time findings, certain immediate modification of the treatment strategy (e.g. a change in the plane of rotation upon perceiving that the nystagmus has converted to a different pattern indicating a conversion of canalithiasis from one semicircular canal to another).

For convenience and economy, the system may provide structure to interface with other available systems that are designed to evaluate and/or treat similar disorders (e.g. existing videonystagmography equipment, posturography computers, audiometers, impedance audiometers, evoked response computers, monitors of vital signs, etc.). This interface may be indirect, through the input of the operator, or directly interfaced to the system.

Real-time electronic analysis of nystagmus can be performed by an existing unit inserted into the system, or by a specially designed unit that gives specific information on the axis of rotation, angular direction and velocity of the slow phase, and thereby identify the generating semicircular canal(s).

A special headrest may be provided for presenting the head with appropriate oscillation designed to mobilize intracanalicular dense masses or elicit diagnostic responses. One embodiment of the headrest involves three linear transducers oriented orthogonally to provide oscillation of the headrest, and thereby the head, in any desired direction.

Off board to onboard electrical signals, and onboard to off board telemetry, can be transmitted either by means of FM transmission, slip-rings at points of bearing or hard-wiring wound up on a spindle, or a pair of counter-rolling spindles.

Tasks involved in graviception can be used in both testing and treatment, the difference being, as a general rule, that graviceptual testing withholds immediate feedback, whereas graviceptual treatment purposely provides immediate feedback so that the subjects can recalibrate their perceptive errors. The data display for the gravitational tests and treatments is provided in both on-going and cumulative fashion, and in general provides single-number scores with which comparisons are easily made.

The visual graviception test presents the subject with the task (e.g. using the VGI) of manually orienting a visualized object in the roll and pitch plane to the subject's perceptions of gravitational orientation while the chair is oriented in a variety of positions with respect to gravity. This can indicate, for instance, that a 15-degree roll-tilt of the chair to the right is perceived as 15-degrees, but a similar 15-degree roll-tilt to the left is perceived as only 9-degrees, indicting damage to the utricle, the sensor of roll-tilt, in the left ear.

The sound-altered graviception test (novel) is carried out by having test subjects indicate their perception of gravity orientation in both the roll and pitch planes before and during the presentation of a sound to one ear by earphones. It can thereby be determined, by documenting any difference in the gravitational percept produced under the two conditions, whether the test ear is a source of distorted perception of gravity under conditions of noise, and the intensity and character of the sound required to elicit that response. A similar test can be provided by the presentation, rather than sound, of positive and negative air pressure to the ear canal (the pressure-altered graviception test).

Graviception feedback treatment is carried out by giving the subject a series of graviceptual tasks while also giving constant feedback regarding his/her deviation from the actual gravitation vector. The task can involve an object placed before the subject (e.g. a slightly concave plate with a free ball placed on it, or a translucent sphere with a free ball inside, where the task is to orient the object so that the ball is at a certain point), or similar objects can be projected on the screen in two or three dimensions.

It is often difficult to determine whether a subject's chronic imbalance is due to hypofunction of the otolithic organs, or due to an ongoing distorted dysfunction. In the state-of-the-art, an off-vertical axis rotation (OVAR) test supposedly provides a diagnostic method for the purpose of ruling out, or validating, otolithic hypofunction. By isolating the function of the otolith organs from the semicircular canals, the test is designed to exclusively assess whether or not the otolith organs are functioning. OVAR testing can be carried out in two distinctly separate ways. The first way involves placing the subject on a rotateable chair in the earth-vertical axis, then rotating the chair at a constant velocity until nystagmus has ceased, due to the VOR no longer reacting to the angular acceleration at onset. Then the chair is tilted off-axis, bringing the utricles into play. If the subject then demonstrates renewed nystagmus, this is considered to be due to functioning utricles. The imparted maneuver does not involve angular acceleration. If renewed nystagmus is not seen, the utricles are considered to be hypofunctional. But the validity of this test is questionable due to the fact that the subject may be subconsciously suppressing either otolithic function or nystagmus, thereby giving a false positive. My research indicates that this test often gives a false positive conclusion for otolithic hypofunction for this reason, which infers that treatment of the labyrinth is hopeless in the subject, when in fact it is not.

The second form of OVAR test, recently described by Dornhoffer, et al, consists of rotating the subject in an off-vertical axis manner while having the subject indicate the percept of the visual subjective vertical. The degree of deviation of the percept from the actual earth-vertical is a correlate of otolithic hypofunction. Placing the axis at each ear independently provides lateralization information, because only the non-axial ear is subject to centrifugal force. But this form of the test depends upon only a subjective, behavioral response, which fact clouds the validity of the test.

Not only can both forms of these OVAR tests be carried out with the present invention, but they can be carried out simultaneously, creating a novel test of greater reliability and validity than the two tests accomplished separately. This combined test has the advantages of objectivity, through testing for otolithic-actuated nystagmus without semicircular canal involvement while at the same time providing a means to prevent, through a subjective response, a false positive conclusion of hypofunction because of nystagmus suppression. In addition, the attention required to undertake the objective task tends to inhibit suppression of nystagmus.

Another useful test provided by the present invention is the dynamic visual acuity test, which involves testing the subject during passive head rotation as he/she attempts to read written material that is fixed to the earth-bound surround. This is a test of the VOR system's ability to prevent slip of the retinal image under these conditions. Hypofunction of the VOR will be demonstrated during rotation by a loss of visual acuity, and the display, in the ocular monitor, of "make-up" saccades that the subject utilizes to make up for the retinal image slip. This is done by either leaving one eye exposed to the screen carrying the written material while the other eye is monitored with the camera, or by using semi-reflective mirrors. This test can be done without the present invention, but by providing motion control and computerized analysis a much more accurately quantified test is provided.

The present invention also provides a capability to carry out impulsive or ramp testing of individual semicircular canal function. This test makes use of the fact that the primary afferents from a normal semicircular canal are driven into inhibitory saturation by rapid, unexpected, passive acceleration and/or deceleration of the head in the plane of the canal and in the direction of inhibition. This fact is normally compensated by the opposing, opposite, complementary semicircular canal, which anatomically moves in the excitatory direction during the same movement. But, if the opposing canal is hypofunctional, there is a resulting momentary loss of VOR function so that the eyes will lose their fixation on an earth-stationary subject, and will demonstrate a compensatory saccadic movement back to the fixation point immediately after the head movement. The amplitude of the saccade is an indicator of loss of VOR function of the stimulated semicircular canal. The impulsive or ramp movements of the head can be provided by the positioning apparatus, and the optical analysis performed by the video-camera/scanning/analysis system inherent in the invention. Impulsive movements are angular movements that start and stop suddenly, ramp movements begin more slowly, then stop suddenly. Impulsive testing of individual semicircular canal can be done clinically, without sophisticated equipment, but involves sudden twisting of the head that invokes risk in some subjects. The present invention avoids that risk.

Because the amount of acceleration-deceleration of the head must be great to perform the impulse/ramp test, and the present apparatus can only apply angular acceleration to the whole body, an impulse of this magnitude applied to the whole body would require great power. For this reason, a ramp movement can be used, whereby the positioning apparatus accelerates (angular motion) slowly, but can unexpectedly come to a rapid stop as a result of the breaking mechanism in the apparatus. Ramp testing requires the positioning apparatus, and requires data-stream coordination between acceleration/positional input and optical output, and is a novel feature of the present invention. On the headgear or goggles, one eye is left exposed to a visual image that is fixed to the positioning apparatus, while the other is monitored by the camera. The subject's task is to obtain and then maintain fixation on the image, which is earth-fixed. When moving toward a weak canal in the plane of movement, the sudden stop will evoke a saccadic (quick) movement as the eye, having momentarily lost the image fixation, quickly regains fixation on the image.

The novel arrangement of the various components in this assembly provide flexibility and convenience. Thus, the multi-axial positioning chair requires minimal space, the balanced design requires less powerful motors, the suspension design for support of the moving parts requires minimal weight, and the spherical screen with its focal point always located at the subjects' head remains equidistant in all aspects from the rotating subject and thereby provides no unwanted spatial orientation cues.

The curved-shaped screen is for the purposes of displaying projected images, the isolating the subject from the visual surround and providing darkness so as to prevent visual fixation effects which tend to suppress nystagmus. A stationary portion covers approximately 180-degrees on the side opposite to the entry side, and a second moveable portion rotates with the first axis and prevents the ingress of ambient light when the subject is oriented so as to face toward the stationary screen.

The basic processes of the system begin first with securing the subject in the chair with appropriate restraints, including securing the head in the headrest, and then indicating, for calibration purposes, the approximate angle of the tragal-canthal line to the pitch plane, which anatomically represents the plane of the horizontal semicircular canals in relation to the pitch plane. It also indicates the null position for non-zero-buoyant cupulae. When the subject is in the seated position, the pitch plane orientation of the tragal-canthal line will vary significantly from subject to subject depending upon other anatomical factors. This calibration can be accomplished by placing a pitch plane calibration line on a calibration apparatus, near the eye-level and to the side of the subject, with the calibration apparatus articulating so that it allows adjustment in the pitch plane. This setting can be entered into the software as a calibration adjustment, or the act of adjusting the pitch of the calibration unit can directly set the plane of the pitch plane gravity sensor. This plane, then, represents the pitch plane null angle for that subject during that session.

Alternatively, the chair can be rotated in the pitch plane so as to place the tragal-canthal line perpendicular to the axis of the suspending frame, and thus perpendicular to the earth vertical vector, and thenceforth all testing is carried out on this subject with the chair angle thus fixed with relation to the suspending frame. With this reference, the primary upright position of the head is arbitrarily set at 30-degrees posterior to the null angle in the pitch plane, and all stated angles thenceforth are based upon on the primary position representing zero degrees in the pitch, roll and yaw planes. However, the option is given of basing all stated angles on the null position.

The process for the system to carry out the basic and pathognomonic test for benign paroxysmal positional vertigo, called the Dix-Hallpike Maneuver when carried out manually with the subject placed on a table, is as follows.

Beginning with the seated subject's head placed in the neutral position, or null angle, and after allowing for at least 10-seconds after any prior move, any spontaneous nystagmus is then recorded over the next 10-seconds, noting the axis of rotation (AOR), fast phase direction (FPD) and slow phase velocity (SPV) of the nystagmus. The chair is rotated 45-degrees in the yaw plane to the side undergoing testing, 5-seconds allowed for cessation of rotation-induced nystagmus, then rotated backward in the pitch plane 120-degrees at a rate of 20-degrees per second, with a buffered stop. After 2-seconds, the eyes are monitored for 20-seconds for one or more of the following nystagmus responses:

1) Torsional nystagmus with the AOR offset 30-degrees to the test side and the direction of fast phase rotation such that the superior pole of the eyeball moves toward the test side (CCW for the right side);
2) Horizontal nystagmus with its SPV more than 8-degrees per second after adjusting for any spontaneous nystagmus that was noted in the null position (the slow SPV of the spontaneous nystagmus, if horizontal, is added or subtracted from the SPV of the present nystagmus);
3) Nystagmus of essentially the same character (in regard to its plane/axis, FPD and SPV) as noted in the neutral position;
4) Other nystagmus;
5) No significant nystagmus.

If response #1 occurs, the observation time window continues another 30-seconds, or until the nystagmus slow phase eye speed reaches 10% of its maximum reached during the first window, whichever is less. If response #1 occurs, but ceases before the end of 20-seconds, the test is classified as "POSITIVE, typical nystagmus response to test maneuver for posterior canal canalithiasis" for that side.

If response #2 occurs, the result is classified as "horizontal canal canalithiasis, or cupulolithiasis, or lithiasis jam; go to tests for horizontal lithiasis".

All other responses are classified as "negative response" for that side, but a report of the particular response is recorded. For #1 or #2 responses, the latency and duration of the response is noted, plus the attack rate (time of onset until maximal SPL is reached).

The chair is then rotated 45-degrees toward the non-test side, at 10-degrees per second, delayed for 1.5-seconds, then forward in the pitch plane to the neutral position. After allowing 2.0-seconds for any rotation-induced nystagmus to clear, any nystagmus response is noted that occurs within a 15-second time window. If, during that window, significant (SPV greater than 2-degrees per second) nystagmus response occurs with the same axis offset direction but reversed FPD, the test is further classified as "confirmed positive response of typical nystagmus (reversal of FPD on return to upright.

Procedure for Canalith Repositioning

The treatment of choice for classical benign paroxysmal positional vertigo (BPPV) of the posterior semicircular canal is called the canalith repositioning procedure. This and related maneuvers for variations of benign paroxysmal positional vertigo (BPPV) are called repositioning maneuvers, and are also known as the "Epley Maneuvers". These are all generally carried out manually with the subject placed on a table. The disadvantages of carrying out these procedures manually are as follows:

1) It involves twisting and stretching the neck back, which is a hazard in subjects with neck and back problems.
2) The eyes are not easily visualized in the various positions. It is a basic tenet of the procedure that the eyes be constantly monitored with regard to nystagmus during the procedure in order to determine the timing of the positioning sequence, and to detect any nystagmus that indicates the development of a canalith jam or an conversion to another canal and thus indicates the need for a change in strategy.
3) In a portion of cases, there the need for the performance of a 360-degree maneuver in the pitch or roll plane, which maneuvers are difficult and potentially risky to carry out on a table or without some form of positioning apparatus for the subject.

These disadvantages are avoided by carrying out the procedure with the present vertigo management system. The process for the system to carry out treatment of benign paroxysmal positional vertigo by repositioning maneuvers follows. It presumes that the diagnosis and localization of pathology via the Hallpike maneuver, as performed by the system of the present invention as described above, has already taken place. The latency, duration, axis of rotation (AOR), fast phase direction (FPD) and slow phase velocity (SPV) of the nystagmus are duly noted from the prior procedure. For illustration, the procedure will be described that would apply to canalithiasis (free particles) in the posterior semicircular canal on the left. (Treatment of canalithiasis of the right posterior semicircular canal would involve a mirror image procedure.)

Beginning with the seated subject's head placed in the neutral position, or null angle (30-degrees forward, 0-degrees to side), and after allowing for at least 30-seconds after any prior move, any spontaneous nystagmus is then recorded over the next 10-seconds, noting the axis of rotation (AOR), fast phase direction (FPD) and slow phase velocity (SPV) of the nystagmus. The head is rotated 45-degrees in the yaw plane to the left, 5-seconds allowed for cessation of rotation-induced nystagmus, then rotated backward in the pitch-roll plane 120-degrees at a rate of 20-degrees per second, with a buffered stop. The display reports "Position #1". After 2-seconds, the eyes are monitored for 30-seconds for one or more of the following nystagmus responses, noting the axis of rotation (AOR), fast phase direction (FPD), slow phase velocity (SPV) of the nystagmus at its maximum, the latency and duration of the response, plus the attack rate (time of onset until maximal SPL is reached. This information is also obtained at each subsequent sequential position, and the following responses noted.

1) Torsional nystagmus with the AOR offset 15–45-degrees to the left and the direction of fast phase rotation such that the superior pole of the eyeball moves toward the left (clockwise as seen by the observer), and an attack rate of less than 8-seconds;
2) Horizontal nystagmus with its SPV more than 8-degrees-per-second after adjusting for any spontaneous nystagmus that was noted in the null position (the slow SPV of the spontaneous nystagmus, if horizontal, is added or subtracted from the SPV of the present nystagmus);
3) Nystagmus of essentially the same character (in regard to its plane/axis, FPD and SPV) as was noted in the neutral position;
4) Other nystagmus;
5) No significant nystagmus.
6) Response as in #1 except with attack rate greater than 8-seconds.

If response #1 occurs, the latency and duration of the response is noted, plus the attack rate (time of onset until maximal SPL is reached). The observation time window remains open and the position is maintained for 60-seconds, or until the slow phase velocity of the nystagmus decreases to 10% of its maximum, whichever is less.

If response #2 occurs, the result is reported in the display as "Horizontal canal canalithiasis or cupulolithiasis, or lithiasis jam; go to tests for horizontal lithiasis", and the procedure is aborted.

If responses #3, 4 of 5 occur, the notation in the display is "Typical nystagmus not noted, but recommend proceeding with maneuvers based on prior determination."

If response #6 occurs, the display reports: "Cupulolithiasis suspected. If this sequence is not successful in clearing nystagmus, advise cupulolithiasis protocol."

The head is then rotated in the yaw plane, moving to Position #2 (45-degrees toward the right side, 120-back) at 10-degrees per second. The display reports: "Position #2". The observations and responses to be noted are the same as for Position #1.

The head is then moved at a rate of 10-degrees per second in the pitch-roll plane to the 90-degrees back, 45-degrees right position, and then, after no delay, rotated in the yaw plane to 135-degrees right (90-degrees right), to position #3. The display reports "Position #3". The observations and responses to be noted are the same as for Position #1.

The head is then moved at a rate of 10-degrees-per-second in the roll plane to the 90-degree right position, then, without delay, is moved in the roll plane to the 30-degree forward position (still at 90-degrees right), then without delay, rotated to the left in the yaw plane to 0-degrees.

The display then reports: "Repositioning sequence accomplished, advise repeat. Use oscillation applied to left mastoid process unless patient is nauseated". The sequence is repeated if, at any time during just completed the sequence, a #1 response was noted. If, at any time during the sequence of positions #2 through the final position, the nystagmus reverses as indicated by reversal of the FPD compared to the FPD in position #1, the display reports: "Repositioning sequence accomplished, reversal of nystagmus noted indicating failure, advise repeat but using 360-degree maneuver in the plane of the left posterior canal."

The second and subsequent sequences are carried out with oscillation applied to the left mastoid area, unless nausea is encountered. The operator has the option to abort the procedure at any point. Severe nausea is a cause to abort the procedure.

Following a sequence without a #1 response, the procedure is terminated, and the display reports, "Repositioning sequence accomplished. Procedure terminated. Advise usual post-procedure precautions".

It should thus now be quite evident that the unique computer-based system and methodology of this invention make extensive contributions to the art of investigating and treating dizziness-causing vestibular behavior.

Through the use of various appropriate sensors, such as linear and angular accelerometers, video cameras whose outputs are directly viewed and also monitored as data-streams by a computer, controllable and monitorable subjective input devices and selectable denormalization structures and processes, and one or more visual display screens, the subtle, complex, and often illusive real-time intertwinings of dynamically varying outward evidences of vestibular misbehavior are presented for quick, precise, and intuitive visual recognition. Correlative pictorial gathering of subject spatial orientation, along with various ones of these evidences, specially arm the physician, or other involved party, to detect and treat vestibular issues with a great deal of flexibility, versatility, speed, and accuracy. As one can readily tell, the system and method of the present invention uniquely enable and promote comprehensive vertigo management by an appropriately trained and skilled party, with that party, if so inclined, conducting substantially all "management" activities with reference principally to a rich and integrated visual screen display, and to a related computer mouse, or other computer control device.

Variations and modifications, beyond those specifically pictured, described and suggested, are recognized to be possible, and to be discernible by those generally skilled in the relevant art. Accordingly, and without departing from the spirit of the invention, these variations and modifications are believed to be fully embraced by the several claims to invention which now follow.

I claim:

1. A method for observing and identifying abnormal human vestibular activity, where said observing and identifying are promoted by the selective, direct provision, for visual scrutiny, of imagery which effectively directly pictures selected physical and physiologic conditions of a human subject whose vestibular behavior is being observed, said method comprising inducing such activity in a subject through invoking a selected spatial orientation for the subject, and while so inducing, and in preparation for employing a participating computer for processing purposes, creating a viewable, pre-computer-processed, and pictorially representational visual correlation, in the form of imagery on the screen of a display device, which simultaneously pictures current subject spatial orientation along with at least one visually observable motion component of current subject vestibular activity.

2. A method employable in relation to a chosen human subject, and during a period of position-related vestibular activity, for acquiring medically informative data, including computer-processible data, regarding the nature of a selected component of such activity, said method comprising utilizing a sensor device which produces a data-stream that relates to spatial orientation, acquiring, during such a period, first-category data which contains information that effectively describes the de facto pattern and current condition of the chosen subject's spatial orientation, additionally, during that same period, and employing another device which produces a data-stream that relates to subject behavior, acquiring second-category data which contains information that effectively describes the pattern and current condition of at least one selected type of the chosen subject's outwardly expressed behavior which is linked to the selected component of vestibular activity, and supplying the first and second acquired data categories to data processing structure which includes an appropriate computer processor.

3. The method of claim 2, wherein the selected component of vestibular activity includes at least one of (a) nystagmus activity, and (b) otolithic-organ activity.

4. The method of claim 3 which, where the selected component of vestibular activity is nystagmus activity further includes denormalizing a relevant portion of nystagmus-related sensory perception capabilities.

5. The method of claim 4, wherein said denormalizing involves at least one of (a) modifying of the subject's visual perception capabilities utilizing light-occluding goggles, (b) modifying the subject's visual perception capabilities utilizing a spaced surface expanse containing a contrived virtual image of surroundings, (c) presenting a contrived, selectively oriented, apparent or real three-dimensional image for viewing by the subject, (d) introducing selected sounds to at least one of the subject's ears, (e) exposing at least one of the subject's ears to a pressure which is other than normal atmospheric pressure, (f) subjecting the subject's head to vibration, (g) employing a caloric approach by subjecting at least one of the subject's inner ears to temperature variation via introducing fluid to the ear, (h) applying selected electrical voltage to the subject's head, and (i) introducing angular acceleration in the plane of a semi-circular canal.

6. The method of claim 3 which further comprises inducing position-related vestibular activity via establishing subject spatial orientation through a spatial-maneuvering device which is controllable by the computer processor to produce at least one of selected angular positioning, and selected linear positioning.

7. The method of claim 6, wherein the spatial-maneuvering device enables infinite angular orientation of the chosen subject around the three, orthogonal, spatial axes.

8. The method of claim 3 which further comprises inducing position-related vestibular activity via establishing subject spatial orientation through hand-maneuvering of the subject.

9. The method of claim 3 which, where the selected component of vestibular activity is otolithic-organ activity, further includes denormalizing a relevant portion of otolithic-organ-related sensory perception capabilities.

10. The method of claim 9, wherein said denormalizing includes at least one of (a) modifying of the subject's visual perception capabilities utilizing light-occluding goggles, (b) modifying the subject's visual perception capabilities utilizing a spaced surface expanse containing a contrived visual image of surroundings, (c) presenting a contrived, selectively oriented, apparent or real three-dimensional image for viewing by the subject, (d) introducing selected sounds to at least one of the subject's ears, (e) exposing at least one of the subject's ears to a pressure which is other than normal atmospheric pressure, (f) subjecting the subject's head to vibration, (g) employing a caloric approach by subjecting at least one of the subject's ears to temperature variation via introduced fluid to the ear, (h) applying selected electrical voltage to the subject's head, and (i) introducing angular acceleration in the plane of a semi-circular canal.

11. The method of claim 3 which further comprises furnishing at least one image-display zone which is operatively associated with the computer processor, and producing in that zone correlative visual imagery, including pictorial imagery, which provides an instantaneous visual link in time effectively between (a) the de facto chosen subject's spatial orientation, and (b) the contemporaneous state of that subject's behavioral response which relates to the mentioned at least one selected type of outwardly expressed behavior.

12. The method of claim 11, wherein the pictorial imagery includes componentry which is at least one of (a) surrogate-representative of the subject's anatomical structure, and (b) camera derived.

13. Apparatus useable in relation to a chosen human subject for acquiring medically informative data, including computer-processible data, regarding the nature of a selected component of position-related vestibular activity which exists during a pre-selected time period, said apparatus, comprising chosen-subject manipulation structure for establishing different spatial orientations (positions) for a chosen subject, first data-stream structure operatively associated with said manipulation structure, operable, during the mentioned pre-selected time period, to provide computer employable first-category data which contains information that effectively describes the then de facto pattern and current state of the chosen subject's spatial orientation, and second data-stream structure operatively associated with the chosen subject, operable, also during the mentioned pre-selected time period, to provide second-category data which contains information that effectively describes the pattern and current state of at least one selected type of the chosen subject's outwardly expressed behavior which is linked to the selected component of vestibular activity.

14. The apparatus of claim 13 which further comprises a computer processor operatively connected to said first and second data stream structures operable to receive and process such first and second category data, and wherein said computer processor is operatively connected to, and capable of operating, said chosen subject manipulation structure through the use of control algorithm structure at least in part in relation to data received by the processor from said first and second data-stream structures.

15. The apparatus of claim 13, wherein said second data-stream structure is constructed to gather and communicate vestibular-system information relating to at least one of (a) the chosen subject's nystagmus-related activity, and (b) the chosen subject's otolithic-organ-related activity.

16. The apparatus of claim 15 which further includes structure employable selectively to denormalize at least a portion of the chosen subject's sensory perception capabilities as related to at least one of the two, specifically mentioned (a) and (b) categories of vestibular activity.

17. The apparatus of claim 15 which further comprises visual display structure operatively connected to said first and second data-stream structures, operable to produce, effectively therefrom, correlative visual imagery, including pictorial imagery, which provides an instantaneous visual link, in time, between (a) de facto chosen-subject spatial orientation, and (b) the contemporaneous state of the chosen subject's behavioral response that relates to the at least one selected type of outwardly expressed behavior.

18. The apparatus of claim 17 wherein said computer processor is operatively connected to, and capable of operating, said chosen-subject manipulation structure, and the pictorial imagery provided by said visual display structure includes user-accessible interactive icon components which are user-controllable to effect chosen-subject spatial orientation.

* * * * *